(12) United States Patent
Winsor

(10) Patent No.: US 7,330,532 B2
(45) Date of Patent: Feb. 12, 2008

(54) DUAL ENERGY IMAGING USING OPTICALLY COUPLED DIGITAL RADIOGRAPHY SYSTEM

(75) Inventor: Robin Winsor, Calgary (CA)

(73) Assignee: Imaging Dynamics Company Ltd., Calgary, Alberta (CA)

( * ) Notice: Subject to any disclaimer, the term of this patent is extended or adjusted under 35 U.S.C. 154(b) by 104 days.

(21) Appl. No.: 11/290,602

(22) Filed: Dec. 1, 2005

(65) Prior Publication Data

US 2006/0133571 A1 Jun. 22, 2006

Related U.S. Application Data

(63) Continuation-in-part of application No. 10/636,529, filed on Aug. 8, 2003, now Pat. No. 7,010,092.

(51) Int. Cl.
*H05G 1/64* (2006.01)
*G01T 1/20* (2006.01)

(52) U.S. Cl. ............ 378/98.9; 378/98.3; 250/367; 250/368; 250/370.11

(58) Field of Classification Search ........... 378/98.3, 378/98.8, 98.9, 98.11; 250/367, 368, 370.09, 250/370.11
See application file for complete search history.

(56) References Cited

U.S. PATENT DOCUMENTS

| | | | | | |
|---|---|---|---|---|---|
| 4,076,984 | A | * | 2/1978 | Gromov et al. ............ 250/367 |
| 4,247,774 | A | * | 1/1981 | Brooks ....................... 250/367 |
| 4,626,688 | A | * | 12/1986 | Barnes .................... 250/361 R |
| 5,127,032 | A | * | 6/1992 | Lam et al. .................. 378/189 |
| 5,150,394 | A | * | 9/1992 | Karellas ...................... 378/62 |
| 5,235,191 | A | * | 8/1993 | Miller ..................... 250/486.1 |
| 5,481,584 | A | * | 1/1996 | Tang et al. ................ 378/98.9 |
| 5,550,380 | A | * | 8/1996 | Sugawara et al. ...... 250/370.11 |
| 5,712,890 | A | * | 1/1998 | Spivey et al. ................ 378/37 |
| 5,790,629 | A | * | 8/1998 | Svensson et al. .......... 378/98.7 |
| 6,038,286 | A | * | 3/2000 | Wagli et al. ............... 378/98.3 |
| 6,064,715 | A | * | 5/2000 | Sklebitz et al. .............. 378/37 |
| 6,285,740 | B1 | * | 9/2001 | Seely et al. ................ 378/98.9 |
| 6,353,657 | B1 | * | 3/2002 | Bayrock et al. ........... 378/98.3 |
| 6,936,823 | B2 | * | 8/2005 | Sauvage et al. ............ 250/368 |

(Continued)

FOREIGN PATENT DOCUMENTS

CA 2218127 11/1996

(Continued)

*Primary Examiner*—Allen C. Ho
(74) *Attorney, Agent, or Firm*—Gowling Lafleur Henderson LLP; D. Doak Horne

(57) ABSTRACT

This invention relates to an optically coupled digital radiography method and apparatus for simultaneously obtaining two distinct images of the same subject, each of which represents a different x-ray energy spectrum. The two images may be combined in various ways such that anatomical features may be separated from one another to provide a clearer view of those features or of underlying structures. The two different images are obtained using a pair of scintillators separated by an x-ray filter that attenuates part of the x-ray spectrum of an x-ray exposure such that the first and second scintillators receive a different energy spectrum of the same x-ray exposure. Alternatively, the two different images can be obtained without a filter and with two scintillators made of different fluorescing materials that react differently to the same x-ray exposure.

25 Claims, 5 Drawing Sheets

U.S. PATENT DOCUMENTS

| | | |
|---|---|---|
| 6,973,161 B2 * | 12/2005 | Ohtsuki ........................ 378/57 |
| 2005/0012046 A1 * | 1/2005 | Groh et al. ............. 250/370.09 |
| 2005/0017184 A1 * | 1/2005 | Groh et al. .................. 250/367 |
| 2005/0226376 A1 * | 10/2005 | Yun et al. ...................... 378/62 |

FOREIGN PATENT DOCUMENTS

| | | |
|---|---|---|
| CA | 2254877 | 11/1997 |

* cited by examiner

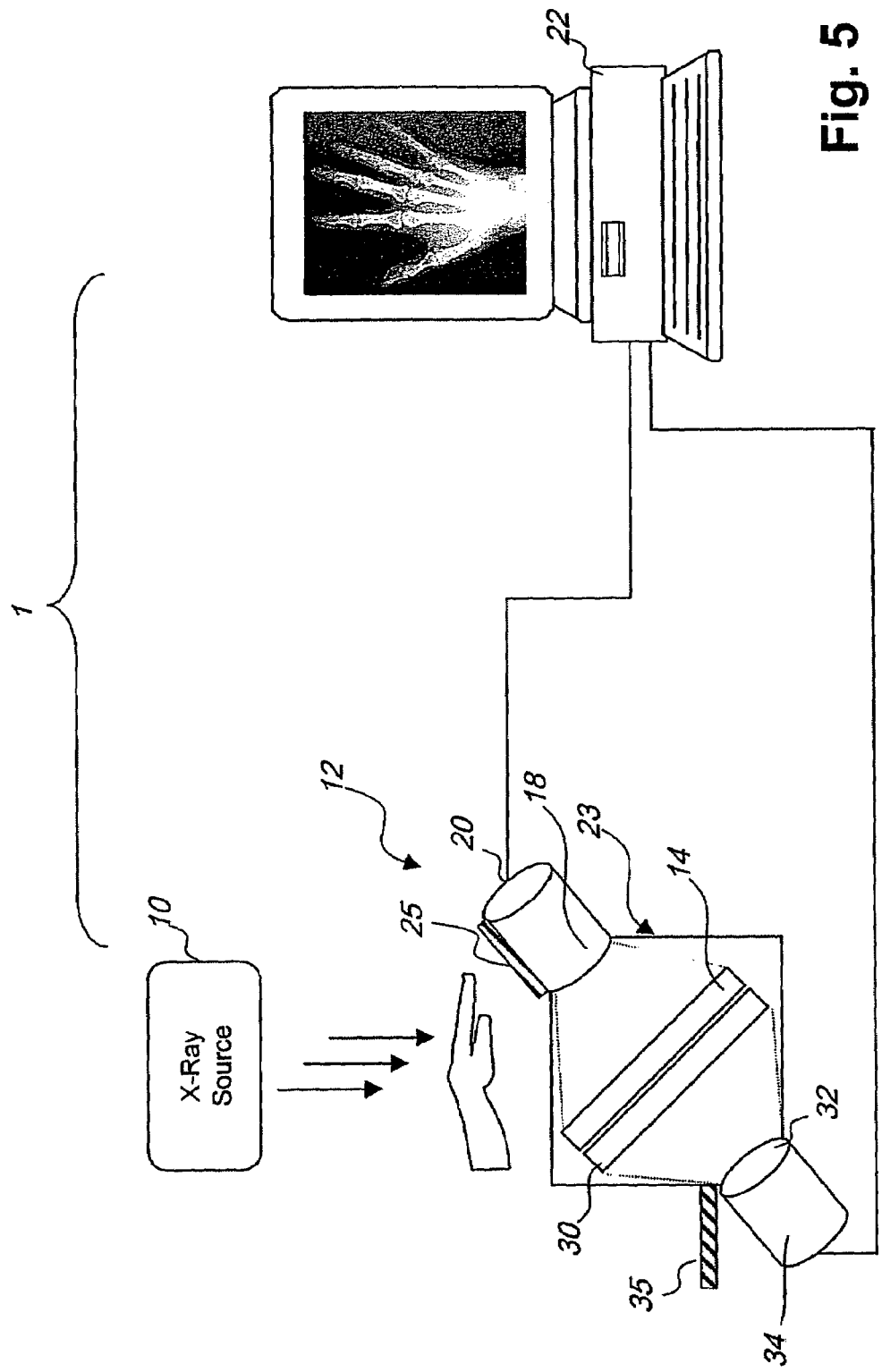

DUAL ENERGY IMAGING USING OPTICALLY COUPLED DIGITAL RADIOGRAPHY SYSTEM

RELATED APPLICATIONS

This application is a continuation-in-part of U.S. application Ser. No. 10/636,529 filed on Aug. 8, 2003, now U.S. Pat. No. 7,010,092 and which is incorporated herein by reference in its entirety and for all teachings, disclosures and purposes.

FIELD OF THE INVENTION

The present invention is directed generally to digital radiography, and in particular to an optically-coupled digital radiography system that can simultaneously acquire two images with different x-ray energy spectra for the purpose of producing separable bone and soft tissue images.

BACKGROUND OF THE INVENTION

For over a hundred years photographic films have been used to capture and display x-rays for diagnostic purposes. In recent years, digital radiography (DR) has become increasingly popular. DR refers to the application of digital equipment and image processing techniques to projection radiography. Digitally recorded x-rays are superior to those recorded with photographic film due to the greater dynamic range offered by a digital recording system. Furthermore, computer image processing techniques provide a wealth of capabilities to study otherwise obscured details within the image.

One type of DR imaging device is an optically-coupled charge-coupled device (CCD) DR system used for clinical diagnosis. Typical optically coupled CCD-based DR systems use a scintillator screen, a mirror and a lens to capture and reduce an x-ray image onto a CCD camera for digitization. To take a digital radiograph using such a system, a DR imaging unit is positioned behind a subject. A standard radiographic generator positioned in front of the subject directs radiation through the subject to a fluorescent-imaging scintillator screen mounted just behind the front surface of the imaging unit. The scintillator screen is the conversion media for radiation to visible light. The scintillator screen absorbs the radiographic radiation and emits light of a particular wavelength which closely matches the peak sensitivity of a CCD camera. A front-surfaced mirror is positioned at an angle inside the imaging unit to direct the visible radiographic image into the CCD camera. The mirror allows the CCD camera to be positioned out of the direct path of the radiation, effectively shielding it from radiation exposure and prolonging its life. A high-efficiency lens is located between the mirror and camera and reduces the image and directs it onto the surface of a CCD sensor in the camera.

The visual image formed by the fluorescent-imaging screen is converted into a digital image by the CCD sensor. A control computer converts the image into a medical image file that can be viewed for clinical diagnosis, enhanced and electronically stored with patient demographic information in a picture archiving system.

Digital radiography has enabled the use of a technique known as dual energy subtraction radiography, which exploits the energy dependence of x-ray attenuation by different tissues. When producing multiple images of a subject obtained by multiple x-ray exposures at different kilovolt peak (kVp) levels and/or by a different filtering of a single x-ray exposure, the photons will interact differently in the scintillator and/or subject. The proportion of photoelectric absorption to Compton scattering will be different in the generation of the different images. Using this effect, a third image can be calculated from the two, in which for instance, the bone structure or soft tissue can be significantly enhanced or suppressed.

One known approach to dual energy digital imaging involves digital imaging devices that use sequential x-ray exposures in rapid succession, at different kVp settings. A scintillator produces multiple images when struck by the multiple x-ray exposures, and these images are captured by a digital sensor for image processing. Because this technique involves multiple sequential exposures, the time delay between exposures tends to cause misregistration resulting in a less-than-perfect separation of the bone and soft tissue components.

Another application of this technique uses a single x-ray exposure detected by two detectors separated by a filter. The filter attenuates a portion of the x-ray spectrum, thereby enabling the detectors to produce two images of the same subject but with different kVp levels, and different contrast properties. Using these two images will make it possible, for instance, to separate the bone structures in one image from the other image, thereby generating a third image that primarily shows soft tissue. Examples of such applications are disclosed in U.S. Pat. No. 4,626,688 (Barnes) and CA 2,218,127 and CA 2,254,877 (Karellas). In Barnes, the detectors are photodiodes that are both located directly in the path of the x-ray exposure, and in Karellas, the detectors are CCD detectors, of which at least one of the detectors are located in the x-ray exposure, along with other components. Disadvantageously, the systems disclosed in both Barnes and Karellas both locate numerous components other than a filter in the path of the x-ray exposure between the x-ray source and the detector. Such non-filter components can corrupt the x-ray image recorded by the detector. Also, both systems locate at least one detector in the direct path of the x-ray exposure, which can be harmful to the detector.

SUMMARY OF THE INVENTION

It is an object of the invention to provide a new dual energy imaging DR system that improves upon known dual energy imaging DR systems. In particular, it is desirable to provide a dual energy imaging DR system with improved imaging accuracy, durability and reduced manufacturing cost.

My invention provides a DR method and apparatus for simultaneously obtaining two distinct images of the same subject, each of which represents a different x-ray energy spectrum. The two images may be combined in various ways such that anatomical features may be separated from one another to provide a clearer view of those features or of underlying structures.

According to one aspect of the invention, there is provided an optically-coupled digital radiography system for simultaneously producing multiple images of differing energies of a subject from a single x-ray exposure of the subject. The system comprises a first and second scintillator, a first and second digital camera, and an x-ray filter. The first scintillator is positioned at an oblique angle to the x-ray exposure and produces a visible first image when subjected to an x-ray exposure of a subject. The first digital camera is positioned out of the path of the x-ray exposure and is optically coupled to the first scintillator for capturing the first image. The x-ray filter is positioned in the path of the x-ray exposure and downstream of the first scintillator, and selectively attenuates a portion of the x-ray spectrum of the x-rays that have passed through the first scintillator. The second scintillator is positioned in the path of and at an oblique angle to the x-ray exposure and downstream of the filter and produces a visible second image when subjected to x-rays that have passed through the filter, wherein the second image is different than the first image. The second scintillator can be positioned substantially parallel to the first scintillator. The second digital camera is positioned out of the path of the x-ray exposure and is optically coupled to the second scintillator for capturing the second image. Advantageously, the first and/or second cameras are optically coupled to their respective scintillators for capturing the respective first and second images directly without reflection from reflection means, such as a mirror or reflective medium interposed between the first camera and first scintillator or second camera and second scintillator. Such an arrangement is particularly desirable to avoid image degradation that may occur as a result of using a reflector.

The filter can be positioned substantially parallel to the first and second scintillators. In particular, the filter can be designed with sufficient mechanical strength to support the first and second scintillators; in which case, the first and second scintillators can be each mounted to respective sides of the filter. The first and second scintillators can have a fluorescing material selected from a large group of known x-ray scintillating materials such as terbium doped gadollineum oxysulfide and thallium doped cesium iodide. The first and second scintillators can each have different fluorescing materials that respond differently to the x-ray exposure, i.e. reacts to a different portion of the x-ray energy spectrum.

Another aspect of the invention has all the components of the above system except for the filter. The differences in the first and second images result from use of two different fluorescing scintillator materials, wherein each material intercepts and reacts to a different portion of the energy spectrum. Suitable scintillator materials include $CaWO_4$, $BaPbSO_4$, BaFCl:Eu, LaOBr:Tm, $Y_2O_2S$:Tb, CsI:Tl, $Gd_2O_2S$:Tb, $BaSrSO_4$:Eu. In order to choose a suitable pair of materials for the scintillators, consideration is given to the portion of the x-ray spectrum to which the materials are most sensitive. By choosing pairs of materials which are as distinct as possible in their x-ray characteristics, the greatest difference will be obtained between the two images. This in turn allows for the least ambiguous separation of the density components by reference to reference tables which chart the possible combinations of bone and soft tissue which can give rise to the observed pixel intensities within the image. One such feasible combination is CsI:Tl and $Gd_2O_2S$:Tb.

According to another aspect of the invention, there is provided an optically-coupled digital radiography system for simultaneously producing multiple images of differing energies of a subject from a single x-ray exposure of the subject. The system comprises first and second scintillators, an x-ray filter, and first and second digital cameras. The first scintillator produces a visible first image when subjected to an x-ray exposure of a subject. The x-ray filter is coated on each side with first and second reflective layers and is positioned in the path of the x-ray exposure and downstream of the first scintillator, for selectively attenuating a portion of the x-ray spectrum of the x-rays that have passed through the first scintillator. The second scintillator is positioned in the path of the x-ray exposure and downstream of the filter and produces a visible second image when subjected to x-rays that have passed through the filter, with the second image being different than the first image. The first digital camera captures the first image, and is located out of the path of the x-ray exposure and is optically coupled to the first scintillator by the first reflective layer. The second digital camera captures the second image, and is located out of the path of the x-ray exposure and optically coupled to the second scintillator by the second reflective layer.

In this system, the second scintillator can be positioned substantially parallel to the first scintillator. In particular, the first and second scintillators can be positioned substantially orthogonal to the x-ray exposure, and the filter can be positioned at an angle to the x-ray exposure such that the images produced by the first and second scintillators are reflected to the first and second cameras, respectively.

The system can further include a first radiation blocking layer positioned in between the first camera and an x-ray source that emits the x-ray exposure. Similarly, the system can further include a second radiation blocking layer positioned in between the second camera and the x-ray source. The first and second radiation blocking layers can be made of lead and serve to block any stray x-rays that may be directed at the cameras.

BRIEF DESCRIPTION OF DRAWINGS

FIG. 5 is a schematic illustration of a mirror-less and filter-less fifth embodiment of a dual energy DR system having a pair of scintillators constructed of different scintillator materials.

DETAILED DESCRIPTION

Figure 1:
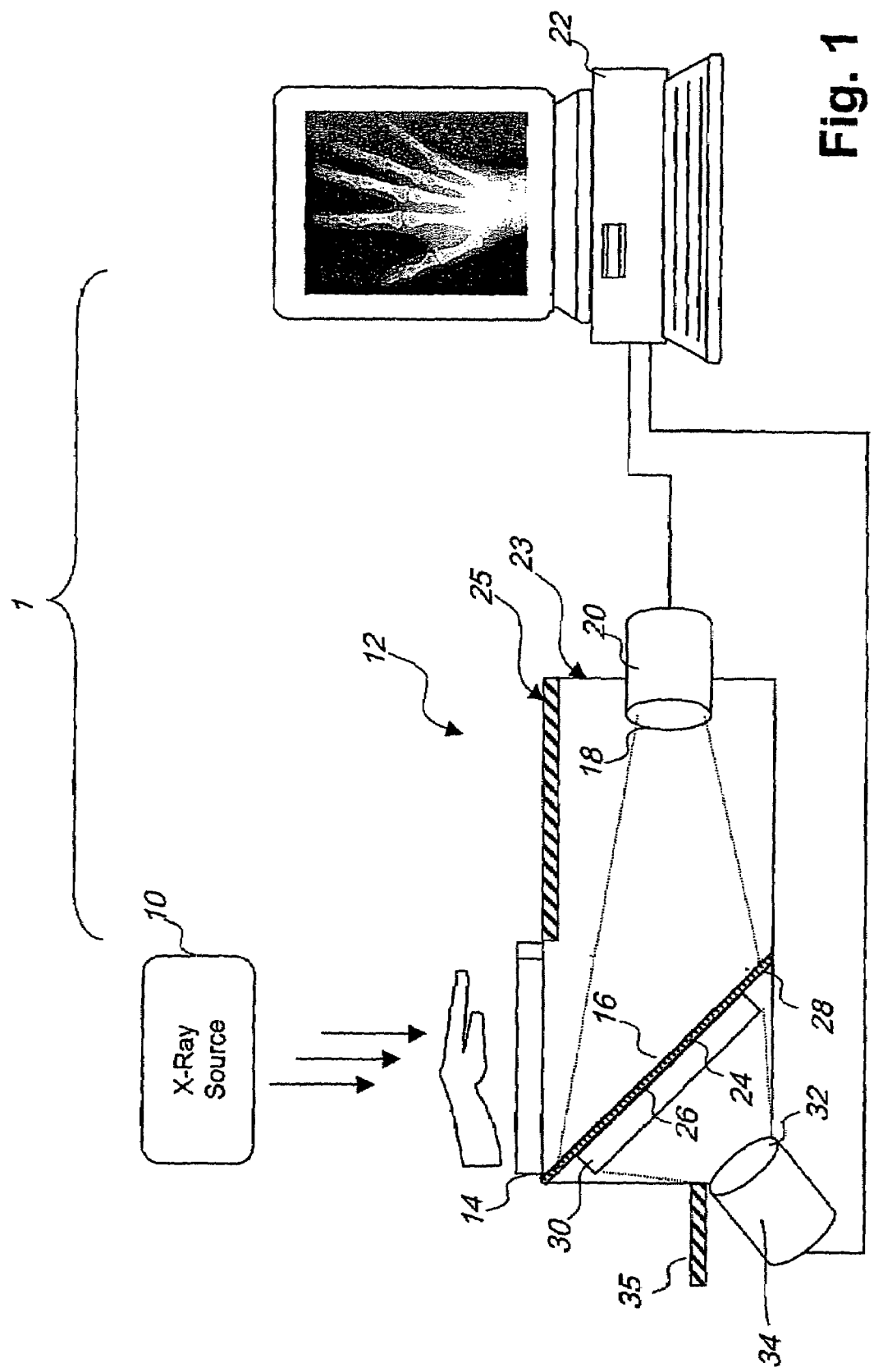
FIG. 1 is a schematic illustration of one embodiment of a dual energy DR system having an x-ray filter interposed between two scintillators constructed of the same scintillator material.

Referring to FIG. 1 and according to one embodiment of the invention, an optically-coupled CCD-based DR system 1 is provided for taking digital x-ray images of a subject, such as a human patient, for clinical diagnostic purposes.

The system 1 is operable to simultaneously obtain two distinct images of a subject, each of which represents a different x-ray energy spectrum. The two images can be algebraically combined in various ways during image processing, such that anatomical features can be separated from one another to provide a clearer view of certain features of underlying structures. In particular, one image can be algebraically combined with another to produce a third image that enhances the bone structure or soft tissue in the subject.

In particular, the two different-energy images obtained by the system 1 can be processed to produce a third image showing only bone or only soft tissue The process uses a set of intensity reference tables provided for each scintillator response to the varying bone/tissue ratios, to identify the actual ratio of bone-to-tissue of the subject in the two images. Once so identified, the system 1 can delete the bone to produce a tissue-only third image, or delete the tissue to produce a bone-only third image. This third image can then be algebraically combined with the first or second image to enhance certain details in those images; for example, a bone-only third image can be subtracted from the first image to suppress the bone detail and enhance the soft tissue detail in the first image. One such image processing method is described in further detail later in this description. However, it is to be understood that other methods known in the art can also be applied to process the two different energy images obtained by the system 1.

The system 1 has an x-ray source 10 that sends x-rays through a subject. When a patient is in position and a part of the patient's body selected for imaging has been set in place, the x-ray source 10 is turned on and x-rays are directed towards the patient. X-rays in a single exposure from the x-ray source 10 pass through the patient and are captured by a detector 12 and converted into two digital x-ray images. In particular, some of the x-rays reaching the detector 12 are first converted into visible light by a first scintillator 14 positioned orthogonal to the x-ray source 10. The visible light forms a visible image which is reflected by a mirror 16 towards lenses in a first lens assembly 18, which reduces and directs the image onto the surface of a first CCD camera 20, which then converts the image into a first digital image. The first digital image is then transmitted to a computer 22 for image processing and storage. The first scintillator 14, mirror 16, first lens assembly 18 and first CCD camera 20 are mounted to a detector housing 23 such that the optical coupling between the first scintillator 14 and first CCD camera 20 is located entirely within the housing 23. In particular, the first scintillator is mounted to the housing such that light generated by the first scintillator 14 projects into the housing 23. The mirror 16 is mounted inside the housing 23 such that light projected by the first scintillator 14 is reflected towards a part of the housing located out of the path of the x-ray exposure; the first lens assembly 18 and first CCD camera 20 are mounted to this part of the housing 23 and receive light reflected by the mirror 16. The inside surfaces of the housing 23 are rendered non-reflective as much as possible in order to prevent stray reflections from reaching the first CCD camera 20.

A portion of the housing 23 between the first CCD camera 20 and the x-ray source 10 is lined with a first radiation blocking layer 25 to shield the first CCD camera 20 from stray x-rays emitted by the x-ray source 10. These stray x-rays do not pass through the first scintillator 14 and for example, may be deflected by air molecules towards the first CCD camera 14. The first radiation blocking layer 25 can be made of lead or another suitable radiation blocking material as known in the art.

The mirror 16 is positioned at an oblique angle to the first scintillator 14 in order to reflect the visible image to the camera 20. In this embodiment, the mirror 16 is positioned at a 45 degree angle to the first scintillator 14, and the first camera 20 is positioned in line of sight of the reflected image and out of the path of the x-ray exposure. Alternatively, the first camera 20 can be positioned at other locations on the housing 23 so long as it is out of path of the x-ray exposure. When the first camera 20 is positioned in such an alternative position, the mirror angle and lens assembly focal point are adjusted accordingly.

The first scintillator 14 is made of a material which fluoresces when struck by x-rays, such as terbium doped gadollineum oxysulfide or thallium doped cesium iodide. There are many other suitable scintillator materials, such as $CaWO_4$, $BaPbSO_4$, $BaFCl:Eu$, $LaOBr:Tm$, $Y_2O_2S:Tb$, $BaSrSO_4:Eu$ and others as known in the art. All emit light during this reaction when they are struck by x-rays.

The mirror 16 comprises an x-ray transparent support layer 24 coated on one major surface with a thin reflective layer 26 and on its other surface with a filter layer 28. In this embodiment, the support layer 24 composition is plastic, the reflective layer 26 composition is aluminum, and the filter layer 28 composition is copper. In particular, the copper filter layer 28 has a thickness of about 0.5 mm; however, any suitable metal filter layer as known in the art may be substituted. Alternatively, the mirror 16 comprises a metal layer that serves as both a support layer and filter layer, and a reflective layer coating one side of the metal layer.

X-rays that are not attenuated by the first scintillator 14 reach the mirror 16. Most of these x-rays pass through the support and reflective layers 24, 26, as these materials have low attenuation characteristics, and reach the copper filter layer 28. The filter layer 28 absorbs most of the lower energy x-rays, such that the x-rays that pass through the filter layer are predominantly high-energy x-rays. In other words, the filter layer 28 serves to "harden" the x-ray beam.

The predominantly high energy x-rays in the hardened beam then continue through the filter layer 28 and reach a second scintillator 30 mounted to the filter side of the mirror 16. In this embodiment, the second scintillator 30 is made of the same material as the first scintillator 14. The x-rays activate the second scintillator 30, causing it to emit a second visible image. As compared to the first scintillator 14, the second scintillator is exposed to more of the predominantly high energy x-rays, and therefore, the visible image produced by the second scintillator 30 ("high energy image") has different contrast properties compared to the visible image produced by the first scintillator 14 ("low energy image").

This high energy image is then reduced by a second lens assembly 32 mounted to the housing 23; the reduced image is then directed onto the surface of a second CCD camera 34 mounted to the end of the second lens assembly 32, which converts the visual image into a second digital image. The second digital image is then transmitted to the computer 22 for imaging processing and storage. The second CCD camera 34 is mounted facing the second scintillator 30 and out of the path of the x-ray source 10. Alternatively, the second camera 34 can be positioned at other locations inside the detector 12 so long as it is out of path of the x-ray exposure. When the camera 34 is positioned in such an alternative position, a second mirror (not shown) can be provided and the second lens assembly focal point can be adjusted accordingly. In each of these cases, the optical coupling between the second scintillator 30 and second camera 34 is located entirely within the housing 23.

A second radiation blocking layer 35 extends from the housing 23 between the x-ray source 10 and second CCD camera 34 to shield the second CCD camera 34 from stray x-rays emitted by the x-ray source 10. The second radiation blocking layer 35 can be made of lead or another suitable radiation blocking material as known in the art.

In this embodiment, the filter layer 28 is in adjacent parallel contact with the support layer 24 and the second scintillator 30 is in adjacent parallel contact with the filter layer 28; however, the filter layer 28 and second scintillator 30 can be positioned differently, so long as they are in the path of the x-ray exposure, e.g. the filter layer 28 and second scintillator 30 can be placed parallel to the first scintillator 14 and orthogonal to the x-ray source 10 (not shown). In this alternative configuration, a second mirror (not shown) is provided to reflect the visible image produced by the second scintillator 30 to the second CCD camera 34. Alternatively and referring to FIG. 3, the second scintillator 30 can be positioned substantially parallel to the first scintillator 14, and the filter layer 28 is interposed between the first and second scintillators 14, 30 at an oblique angle to the x-ray source 10. Also, the filter 28 is coated on both sides with respective first and second reflective layers 16, 27. When the first scintillator 14 is struck with x-rays, it will emit visible light towards the first reflective layer, which then redirects the image to the first camera 20 positioned out of the x-ray path. When the second scintillator 30 is struck with the hardened x-ray exposure, it will emit visible light towards the second reflective layer 27, which then redirects the image to the second camera 34 positioned out of the x-ray path. This arrangement is particularly desirable as the filter 28 serves as a support structure for both of the reflective layers 16, 27, thereby avoiding the extra cost and complexity associated with providing separate support structures for the reflective layers 16, 27 as well as avoiding the possibility that the support layers will interfere with the x-ray beam and corrupt the image produced by the second scintillator 30.

Figure 3:
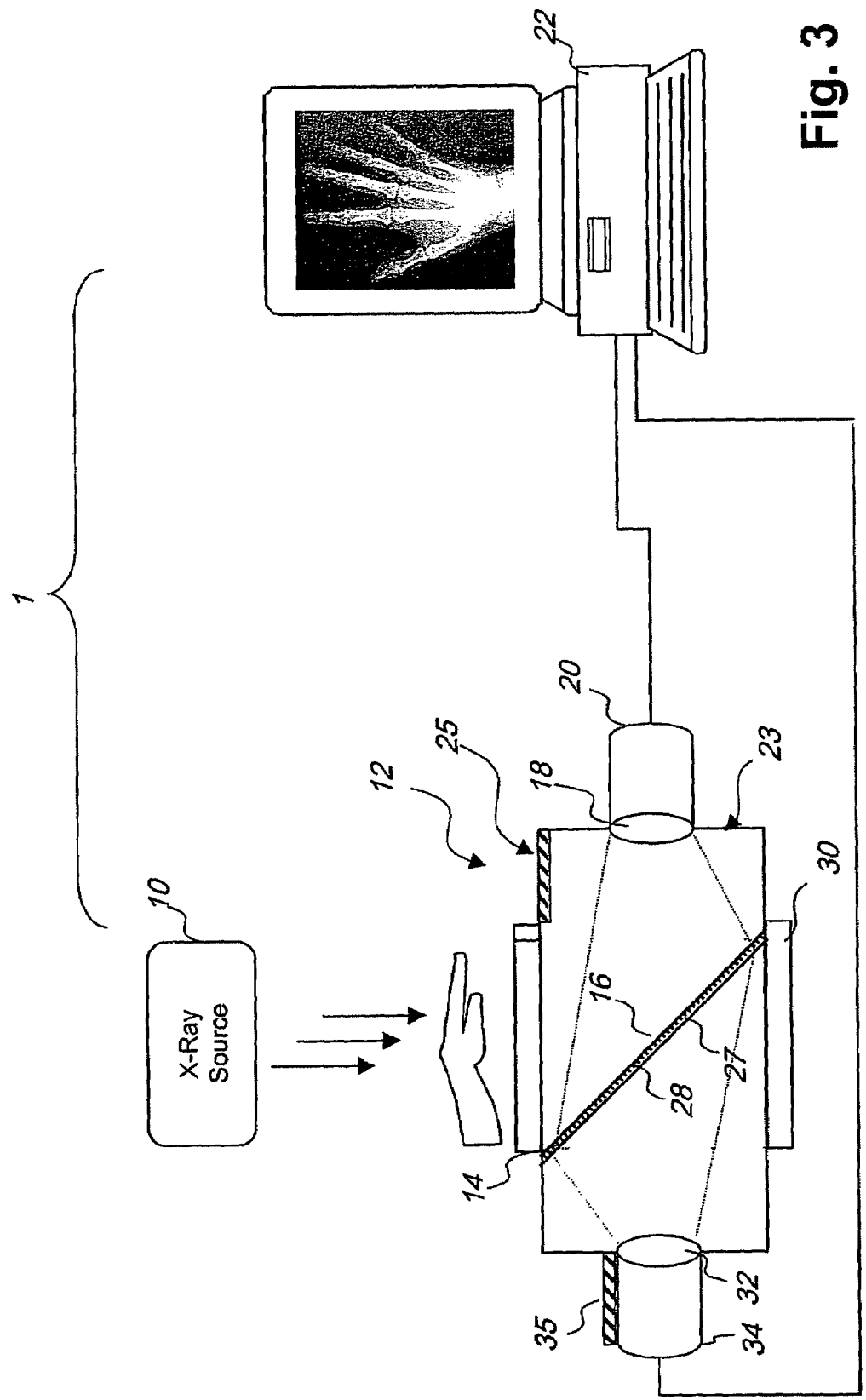
FIG. 3 is a schematic illustration of a third embodiment of a dual energy DR system having an x-ray filter coated on both sides with a reflective layer and interposed between two parallel, spaced scintillators.

In FIG. 3, the cameras 20, 34 are shown mounted horizontally in the system 1 and in-line with each other; alternatively, the cameras 20, 34 can be mounted in different locations in the system 1, so long as they remain optically coupled to their respective scintillators 14, 30 and remain out of the path of the x-ray exposure. For example, the second camera 34 can be mounted on the housing 23 more closely to and directly facing the filter layer 28 or mounted in other positions that produce a more compact system 1. The second scintillator 30 can be constructed as a Lambertian emitter. Lambertian emitters have a luminous distribution that is uniform for all directions in comparison to non-Lambertian emitters from which emissions are more directional. When the second scintillator 30 is a Lambertian emitter, the second camera 34 can be mounted in various positions on the housing and still remain optically coupled to the second scintillator 30. Even though a Lambertian emitter scintillator tends to produce a lower resolution image than a non-Lambertian emitter scintillator of the same dimensions, the resolution of the second image will still be sufficient to usefully enhance images produced during dual energy subtraction processing.

As in the embodiment shown in FIG. 1, the first and second CCD cameras 20, 34 are shielded from stray x-rays by the first and second radiation blocking layers 25, 35.

The x-ray source 10, scintillators 14, 30, lens assemblies 18, 32 and CCD cameras 20, 34 are per se known in the art, and for example, can be those manufactured by Imaging Dynamics Company Ltd for their Xplorer line of detectors.

Once the high and low energy images have been acquired, the computer 22 can then run a program that eliminates the bone or soft tissue components from an image altogether, by using a set of intensity reference tables provided for each scintillator response to the varying bone/tissue ratios to identify the actual ratio of bone-to-tissue of the subject in the two images. The reference tables comprise a set of bone/tissue ratios associated with a set of pixel intensities, and are stored in memory on a computer 22 for use during image processing. The reference tables are constructed from exposures of multiple test subjects. The different test subjects represent different ratios of bone to tissue, and comprise different ratios of a first material such as aluminum to represent bone density, and a second material such as Lucite to represent soft tissue density. The exposures of these test subjects activate a scintillator, which in turn emits visible light for capture by a CCD camera. The intensity of each pixel in each exposure is recorded and associated with the exposed test subject, and thus to the bone-to-tissue ratio associated with that test subject.

To determine the actual bone/tissue ratio of the imaged subject, the computer 22, for each image A, correlates the measured intensity $I_A$ of each pixel $P_{A[i,j]}$ at positions [i,j] in the image A to one or more bone-tissue ratios in the reference map. As there can be multiple bone-tissue ratios for each pixel intensity, the computer 22 compares the associated bone-tissue ratios for the pixel $P_{1[i,j]}$ in the first image to the bone-tissue ratios for the pixel $P_{2[i,j]}$ in the second image. As images 1 and 2 represent the same subject, the bone/tissue ratio common to both images 1,2, will be selected as the actual bone-tissue ratio of the imaged subject. Knowing this ratio, a new image showing only bone or only soft tissue can be constructed. This new image can then be algebraically combined with the first or second image to enhance certain details in those images; for example, a bone-only image can be subtracted from the first image to suppress the bone detail and enhance the soft tissue detail in the first image.

For example, if a pixel $P_1$ at position i,j in the first image has intensity $I_1$, it may be seen from look up table $R_1$ of reference values for a first scintillator to represent either $x_1$ millimeters of bone and $y_1$ millimeters of soft tissue or $x_2$ millimeters of bone and $y_2$ millimeters of soft tissue. Pixel $P_2$ at position i,j in the second image has a different intensity $I_2$ which from the reference table $R_2$ for a second scintillator may represent either $x_2$ millimeters of bone and $y_2$ millimeters of soft tissue or $x_3$ millimeters of bone and $y_3$ millimeters of soft tissue. Given that both pixels $P_1$ and P2 represent the same anatomy, they must represent the same ratio of bone to soft tissue. The correct ratio is therefore the one candidate common to both tables, $x_2$ and $y_2$. Other methods can also be used but all are dependent on having two images of the same subject imaged with different responses to the incident beam. It should be noted that the different response may be due to either a difference in the beam or a difference in the receptor.

Figure 2:
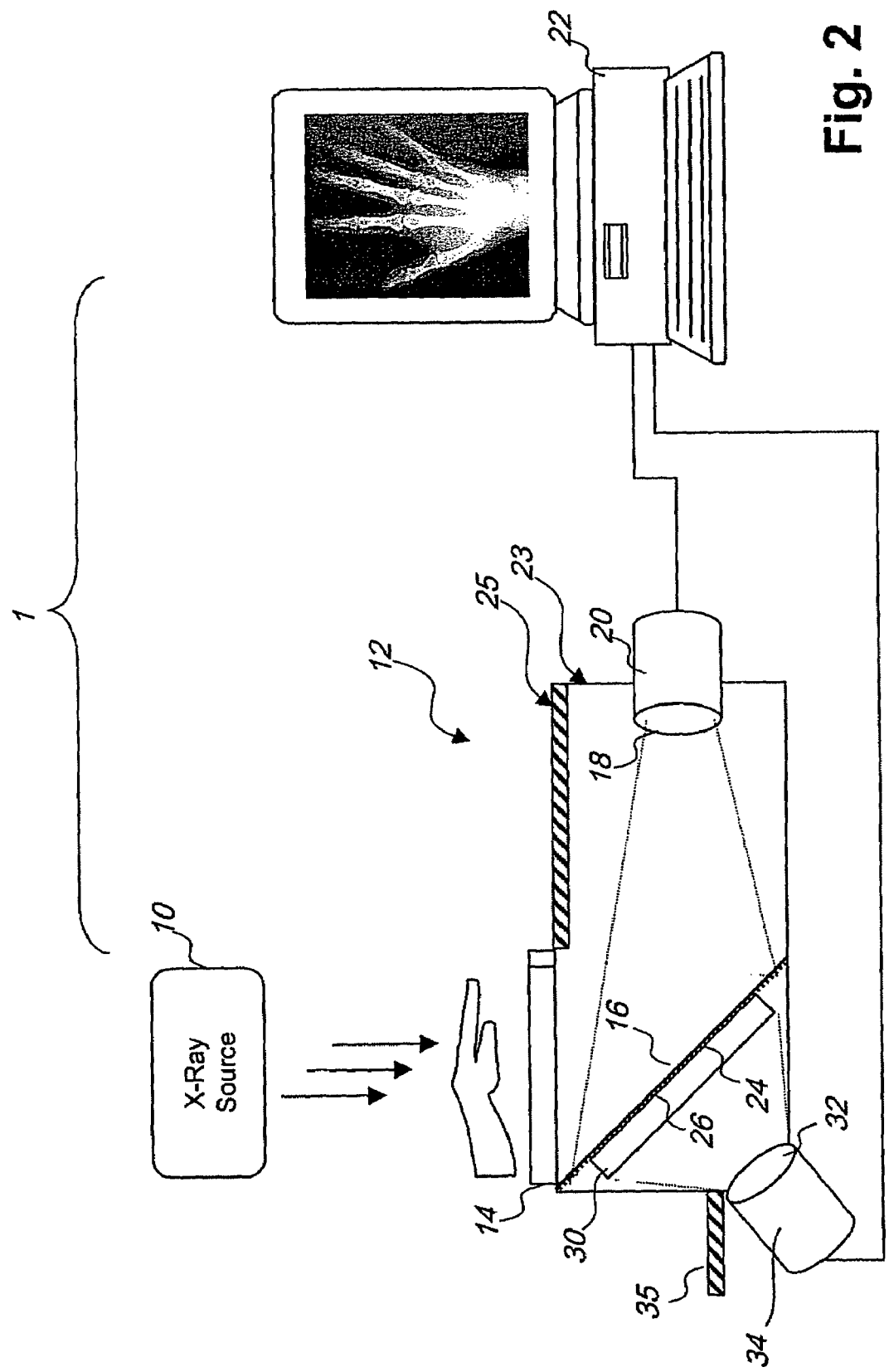
FIG. 2 is a schematic illustration of a filter-less second embodiment of a dual energy DR system having a pair of scintillators constructed of different scintillator materials.

According to another embodiment of the invention and referring to FIG. 2, the system 1 omits the filter layer 28 used in the embodiment shown in FIG. 1 and instead uses different scintillator materials for the two scintillators 14, 30 to produce different visible images. In particular, the first scintillator 14 is composed of thallium doped cesium iodide while the second scintillator 30 is composed of terbium doped gadolineum oxysulfide. The two materials respond differently to the incident x-ray beam and thereby provide the two distinct data sets required for the dual energy separation. The reference tables in the computer are modified to include a set of intensity reference tables for the second scintillator's 30 response to the varying bone/tissue ratios. There are many suitable scintillator materials, such as $CaWO_4$, $BaPbSO_4$, $BaFCl:Eu$, $LaOBr:Tm$, $Y_2O_2S:Tb$, $CsI:Tl$, $Gd_2O_2S:Tb$, $BaSrSO_4:Eu$ and others as known in the art in which pairs of materials may be chosen for the two scintillators 14, 30. In order to choose a suitable pair of materials for the scintillators 14, 30, consideration is given to the portion of the x-ray spectrum to which the materials are most sensitive. By choosing pairs of materials which are as distinct as possible in their x-ray characteristics, the greatest difference will be obtained between the two images. This in turn allows for the least ambiguous separation of the density components by reference to look up tables which chart the possible combinations of bone and soft tissue which can give rise to the observed pixel intensities within the image. The principal factor in determining the difference in absorption of the materials is the atomic number. The photoelectric absorption edge of the material becomes more pronounced as the atomic number of the absorber increases.

Figure 4:
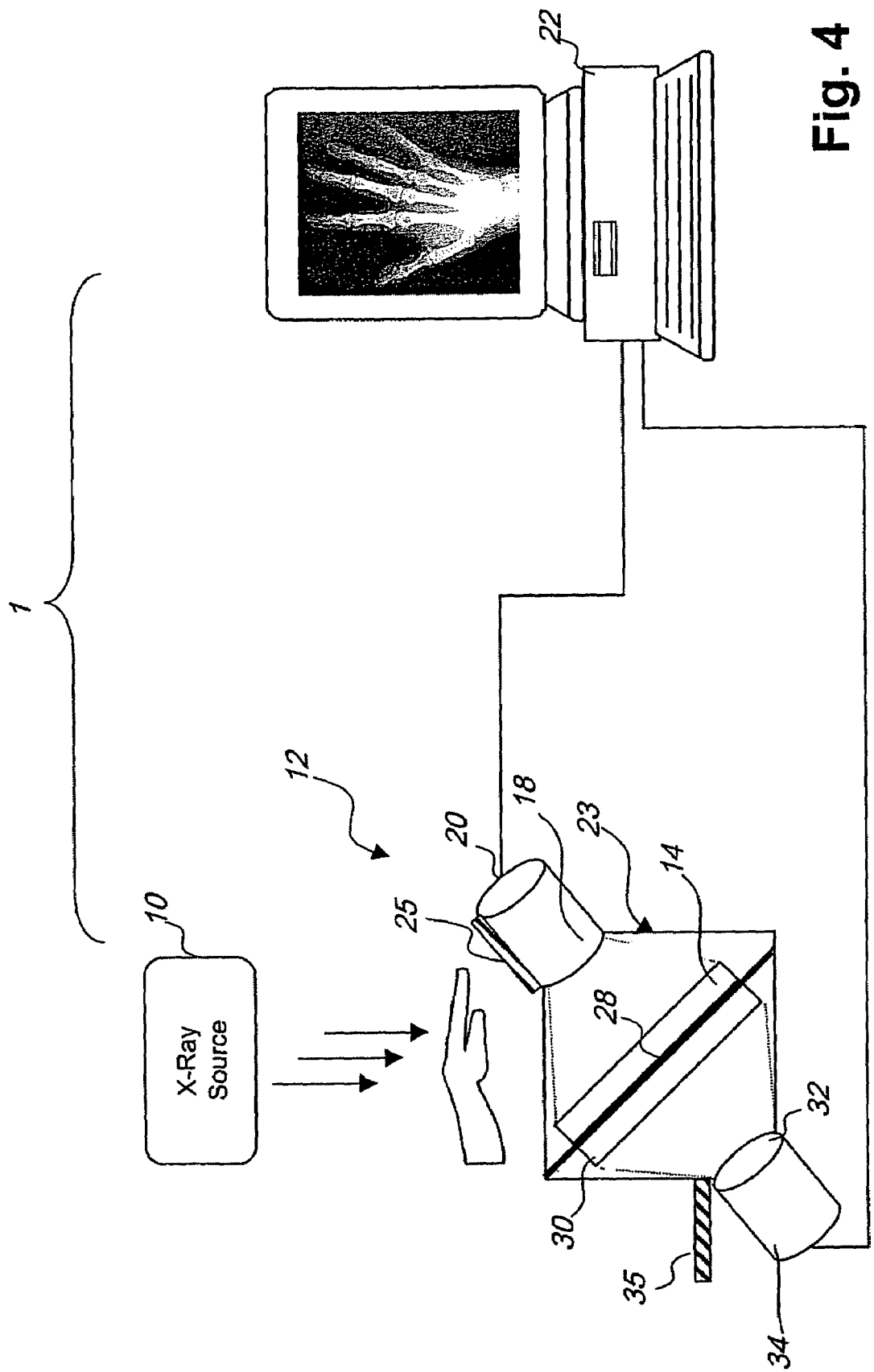
FIG. 4 is a schematic illustration of a mirror-less fourth embodiment of a dual energy DR system having an x-ray filter interposed between two scintillators constructed of the same scintillator material.

According to another embodiment of the invention, and referring now to FIG. 4, the first and second scintillators 14, 30 are respectively mounted to each side of the filter layer 28, such that the scintillators 14, 30 are also angled relative to the x-ray source 10 and substantially parallel to each other. The first lens assembly 18, and digital camera 20 are positioned to face the first scintillator 14, and the second lens assembly 32 and digital camera 34 are positioned to face the second scintillator 30. By arranging the scintillators and cameras in such a manner, the need for a mirror to reflect light from the scintillators 14, 30 to the cameras 20, 34 is avoided. Removing the mirror from the x-ray path reduces the chances that the x-ray exposure will be inadvertently corrupted by a component located in the x-ray path and in between the x-ray source 10 and the scintillators 14, 30. Furthermore, manufacturing costs and system complexity can be reduced by removing the mirror. Also, image quality is preserved by avoiding imaging degradation caused by reflectors.

As in the embodiments shown in FIGS. 1-3, the first and second CCD cameras 20, 34 are shielded from stray x-rays by the first and second radiation blocking layers 25, 35. As shown in FIG. 4, the first camera 20 is mounted to the housing 23 in way that requires the first radiation blocking layer 25 to line the portion of the first camera 20 facing the x-ray source 10. However, it is within the scope of the invention to alter the position of the first camera 20 (e.g. by changing the angle of the first scintillator 14) such that part of the housing 23 is located between the x-ray source 10 and the first camera 20 and the first radiation blocking layer 25 is mounted on this part of the housing 23.

The scintillator materials can be the same for the first and second scintillators 14, 30, as the filter serves to harden the x-ray exposure before reaching the second scintillator 30. According to another embodiment of the invention, and referring to FIG. 5, a filter-less system is provided in which the scintillators 14, 30 are made of different fluorescing materials, in the same manner as disclosed for the second embodiment. Again, such a mirror-less and filter-less system is particularly desirable as system complexity and manufacturing costs can be reduced.

While the preferred embodiment of the invention has been illustrated and described, it will be appreciated that various changes can be made therein without departing from the scope and spirit of the invention. For example, the cameras 20, 34 can be mounted in different locations in the system 1, so long as they remain optically coupled to their respective scintillators 14, 30 and remain out of the path of the x-ray exposure. For example, the first and second cameras 20, 34 can be located substantially horizontal within the system 1. The second scintillator 30 can be a Lambertian emitter to enable the second camera to be positioned in various locations and still remain optically coupled to the second scintillator 30. Alternatively, the position of other elements of the system 1 can be adjusted or additional reflective or focusing elements can be added to ensure the cameras 20, 34 remain optically coupled to the scintillators 14, 30.

What is claimed is:

1. An optically-coupled digital radiography system for simultaneously producing multiple images of differing energies of a subject from a single x-ray exposure of the subject, the system comprising:
   (a) a first scintillator that produces a visible first image when subjected to an x-ray beam that has passed through a subject, the first scintillator being positioned at an oblique angle to the x-ray beam;
   (b) a first digital camera, optically coupled to the first scintillator, for capturing the first image directly without reflection from reflection means interposed between said first camera and said first scintillator, the first digital camera positioned out of the path of the x-ray beam;
   (c) an x-ray filter positioned in the path of the x-ray beam and downstream of the first scintillator, for selectively attenuating a portion of the x-ray spectrum of the x-rays that have passed through the first scintillator;
   (d) a second scintillator positioned in the path of and at an oblique angle to the x-ray beam and downstream of the filter and that produces a visible second image when subjected to x-rays that have passed through the filter, the second image being different than the first image; and
   (e) a second digital camera, optically coupled to the second scintillator, for capturing the second image directly and without reflection from reflection means interposed between said second camera and said second scintillator, the second digital camera positioned out of the path of the x-ray beam.

2. The system of claim 1 wherein the filter, first and second scintillators are positioned substantially parallel to each other.

3. The system of claim 2 wherein the filter has sufficient mechanical strength to support the first and second scintillators, and the first and second scintillators are each mounted to respective sides of the filter.

4. The system of claim 1 wherein the first and second scintillators have a fluorescing material selected from the group of $CaWO_4$, $BaPbSO_4$, $BaFCl:Eu$, $LaOBr:Tm$, $Y_2O_2S:Tb$, $CsI:Tl$, $Gd_2O_2S:Tb$, and $BaSrSO_4:Eu$.

5. The system of claim 4 wherein the first and second scintillators each have different fluorescing materials that respond differently to the x-ray beam.

6. The system of claim 1 wherein the second scintillator is a Lambertian emitter.

7. The system of claim 1 further comprising a radiation blocking layer positioned between the first digital camera and an x-ray source emitting the x-ray beam.

8. The system of claim 1 further comprising a radiation blocking layer positioned between the second digital camera and an x-ray source emitting the x-ray beam.

9. The system as claimed in claim 1 wherein the first digital camera is positioned so as to capture the first image without the first image ever having been combined with the second image.

10. An optically-coupled digital radiography system for simultaneously producing multiple images of differing enemies of a subject from a single x-ray exposure of the subject, the system comprising:
   (a) a first scintillator that produces a visible first image when subjected to an x-ray beam that has passed through a subject;
   (b) an x-ray filter coated on each side with first and second reflective layers and positioned in the path of the x-ray beam and downstream of the first scintillator, for selectively attenuating a portion of the x-ray spectrum of the x-rays that have passed through the first scintillator;
   (c) a second scintillator positioned in the path of the x-ray beam and downstream of the filter and that produces a visible second image when subjected to x-rays that have passed through the filter, the second image being different than the first image;

(d) a first digital camera for capturing the first image, located out of the path of the x-ray beam and optically coupled to the first scintillator by the first reflective layer; and (e) a second digital camera for capturing the second image, located out of the path of the x-ray beam and optically coupled to the second scintillator by the second reflective layer.

11. The system of claim 10 wherein the second scintillator is positioned substantially parallel to the first scintillator.

12. The system of claim 11 wherein the filter is positioned at an oblique angle to the x-ray beam such that the images produced by the first and second scintillators are reflected to the first and second cameras, respectively.

13. The system of claim 10 wherein the second scintillator is a Lambertian emitter.

14. The system of claim 10 further comprising a radiation blocking layer positioned between the first digital camera and an x-ray source emitting the x-ray beam.

15. The system of claim 10 further comprising a radiation blocking layer positioned between the second digital camera and an x-ray source emitting the x-ray beam.

16. The system as claimed in claim 10 wherein the first digital camera is positioned so as to capture the first image without the first image ever having been combined with the second image.

17. An optically-coupled digital radiography system for simultaneously producing multiple images of differing energies of a subject from a single x-ray exposure of the subject, the system comprising:

(a) a first scintillator comprising a first fluorescing material that produces a visible first image when subjected to an x-ray beam that has passed through a subject, the first scintillator being positioned at an oblique angle to the x-ray beam;

(b) a first digital camera, optically coupled to the first scintillator for capturing the first image directly and without reflection from reflection means interposed between said first camera and said first scintillator, the first digital camera positioned out of the path of the x-ray beam;

(c) a second scintillator positioned in the path of and at an oblique angle to the x-ray beam and downstream of the first scintillator and comprising a second fluorescing material that responds sufficiently differently to the x-ray beam than the first fluorescing material to produce a visible second image that is different from the first image; and (d) a second digital camera, optically coupled to the second scintillator for capturing the second image directly and without reflection from reflection means interposed between said second camera and said second scintillator, the second digital camera positioned out of the path of the x-ray beam.

18. The system of claim 17 further comprising an x-ray filter positioned in the path of the x-ray beam and between the first and second scintillators, for selectively attenuating a portion of the x-ray spectrum of the x-rays that have passed through the first scintillator.

19. The system of claim 18 wherein the filter, first and second scintillators are positioned substantially parallel to each other.

20. The system of claim 19 wherein the filter has sufficient mechanical strength to support the first and second scintillators, and the first and second scintillators are each mounted to respective sides of the filter.

21. The system of claim 17 wherein the fluorescing materials for the first and second scintillators are selected from the group $CaWO_4$, $BaPbSO_4$, $BaFCl:Eu$, $LaOBr:Tm$, $Y_2O_2S:Tb$, $CsI:Tl$, $Gd_2O_2S:Tb$, and $BaSrSO_4:Eu$.

22. The system of claim 17 wherein the second scintillator is a Lambertian emitter.

23. The system of claim 17 further comprising a radiation blocking layer positioned between the first digital camera and an x-ray source emitting the x-ray beam.

24. The system of claim 17 further comprising a radiation blocking layer positioned between the second digital camera and an x-ray source emitting the x-ray beam.

25. The system as claimed in claim 17 wherein the first digital camera is positioned so as to capture the first image without the first image ever having been combined with the second image.

* * * * *